US00PP23512P3

(12) United States Plant Patent
Benzur

(10) Patent No.: US PP23,512 P3
(45) Date of Patent: Apr. 2, 2013

(54) ***CORDYLINE* PLANT NAMED 'CORBZR01'**

(50) Latin Name: ***Cordyline* hybrid**
Varietal Denomination: CORBZR01

(75) Inventor: Issachar Benzur, Tirat Yehuda (IL)

(73) Assignee: Mark Jury Nursery (NZ)

( * ) Notice: Subject to any disclaimer, the term of this patent is extended or adjusted under 35 U.S.C. 154(b) by 3 days.

(21) Appl. No.: 13/135,095

(22) Filed: Jun. 24, 2011

(65) Prior Publication Data

US 2012/0331605 P1 Dec. 27, 2012

(51) Int. Cl.
*A01H 5/00* (2006.01)

(52) U.S. Cl. ..... Plt./383

(58) Field of Classification Search ..... Plt./383
See application file for complete search history.

(56) References Cited

PUBLICATIONS

Basiran et al. The progress and Potentials of Mutation Induction in Vegetatively Propagated Plants in Malaysia. FNCA 2002 Workshop on Mutation Breeding.*

* cited by examiner

*Primary Examiner* — Annette Para
(74) *Attorney, Agent, or Firm* — Cassandra Bright

(57) ABSTRACT

A new and distinct *Cordyline* hybrid named 'CORBZR01' is disclosed, characterized by pink striped foliage color, and distinctive clumping growth habit. Plants are compact and bushy, forming weeping foliage. The new cultivar is a *Cordyline* typically suited for ornamental container and landscape use.

1 Drawing Sheet

Latin name of the genus and species: *Cordyline* hybrid.
Variety denomination: 'CORBZR01'.

BACKGROUND OF THE INVENTION

The new cultivar is the result of a chance discovery in a commercial laboratory in Israel. The inventor, Issachar Benzur, a citizen of Israel, discovered the new variety as a single whole plant, chemically induced mutation of the parent variety, *Cordyline* hybrid 'JURred' U.S. Plant Pat. No. 14,224. The known chemical mutagen used was 10 ppm of 6 Benziylaminopurine. The discovery was made in March of 2007.

After selecting and isolating the new cultivar, asexual reproduction of the new cultivar 'CORBZR01' was first performed in the same commercial laboratory by tissue culture in July 2007. In January 2008 the final, stable clone referred to as 'CORBZR01' was selected. 'CORBZR01' has since produced at least 10 generations and has shown that the unique features of this cultivar are stable and reproduced true to type.

SUMMARY OF THE INVENTION

The cultivar 'CORBZR01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CORBZR01.' These characteristics in combination distinguish 'CORBZR01' as a new and distinct *Cordyline* cultivar:

1. Pink striped foliage color
2. Compact, bushy growth habit.
3. Cascading, weeping foliage.
4. Clumping from the base.

PARENTAL COMPARISON

Plants of the new cultivar 'CORBZR01' are similar to the parent, 'JurRed' in most horticultural characteristics. However, 'CORBZR01' differs in having pink striped foliage. Additionally, the new variety produces plants that are shorter and narrower than the parent variety.

COMMERCIAL COMPARISON

Plants of the new cultivar 'CORBZR01' are best compared to the parent variety, due to the unique plant form.

BRIEF DESCRIPTION OF THE PHOTOGRAPH

The accompanying photograph in FIG. 1 illustrates in full color a typical plant of 'CORBZR01' grown in a greenhouse in Watsonville, Calif. This plant is approximately 12 to 18 months old, grown in a 1 gallon pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'CORBZR01' plants grown outdoors in Watsonville, Calif. The growing temperature ranged from 15° C. to 16° C. at night to 15° C. to 32° C. during the day. No artificial light, photoperiodic treatments or chemical treatments were given to the plants. Measurements and numerical values represent averages of typical flowering types.

Botanical classification: *Cordyline* hybrid 'CORBZR01'.
Age of the plant described: Approximately 12 to 18 months.
Container size of the plant described: 1 gallon commercial container.

PROPAGATION

Time to rooting: 10 to 14 days at approximately 15° C. soil temperature, 22° C. air temperature.
Root description: Fine, fibrous.

PLANT

Growth habit: Clump forming, outwardly arching.
Mature height: Approximately 75 cm.
Mature plant spread: Approximately 100 cm.
Growth rate: Slow to Medium.
Stem diameter: Approximately 0.3 cm.
Stem color: Near RHS Brown 200C, with outer margins of stem near Red-Purple 57A.
Stem diameter: Approximately 5 to 8 cm.
Stem length: Approximately 4 to 6 cm.
Branching characteristics: Well-branched, bushy habit.
Leaves per stem: Average 12 to 15.

FOLIAGE

Leaf:
- *Arrangement*.—Alternate, sessile.
- *Average length*.—25 to 30 cm.
- *Average width*.—0.7 to 1 cm.
- *Shape of blade*.—Linear.
- *Apex*.—Accuminate.
- *Base*.—Sheathing.
- *Margin*.—Entire.
- *Texture of top surface*.—Glabrous.
- *Texture of bottom surface*.—Glabrous.
- *Pubescence*.—Non pubescent.
- *Aspect*.—Erect.
- *Color*.—Upper side: Midzone near RHS Brown 200C, with glossy quality. Margin near Red-Purple 57A. Under side: Midzone near RHS Brown 200C. Margin near Red-Purple 57A. Less glossy appearance.

Venation:
- *Type*.—Parallel.
- *Venation color upper side*.—Indistinguishable from overall foliage.
- *Venation color under side*.—Indistinguishable from overall foliage.

Sheath:
- *Average length*.—2 to 5 cm.
- *Average width*.—0.2 to 0.3 cm.
- *Texture*.—Glabrous.
- *Color*.—Midzone near RHS Brown 200C. Margin near Red-Purple 57A.

FLOWER

Flower: Not observed to date.

OTHER CHARACTERISTICS

Seeds and fruits: Not observed to date.
Disease/pest resistance: Neither resistance nor susceptibility to normal diseases and pests of *Cordyline* has been observed.
Temperature tolerance: The new variety tolerates low temperatures to approximately −5° C. and has been observed to tolerate high temperatures to at least 30° C. Plants can tolerate drought.

What is claimed is:

1. A new and distinct cultivar of *Cordyline* hybrid plant named 'CORBZR01' as herein illustrated and described.

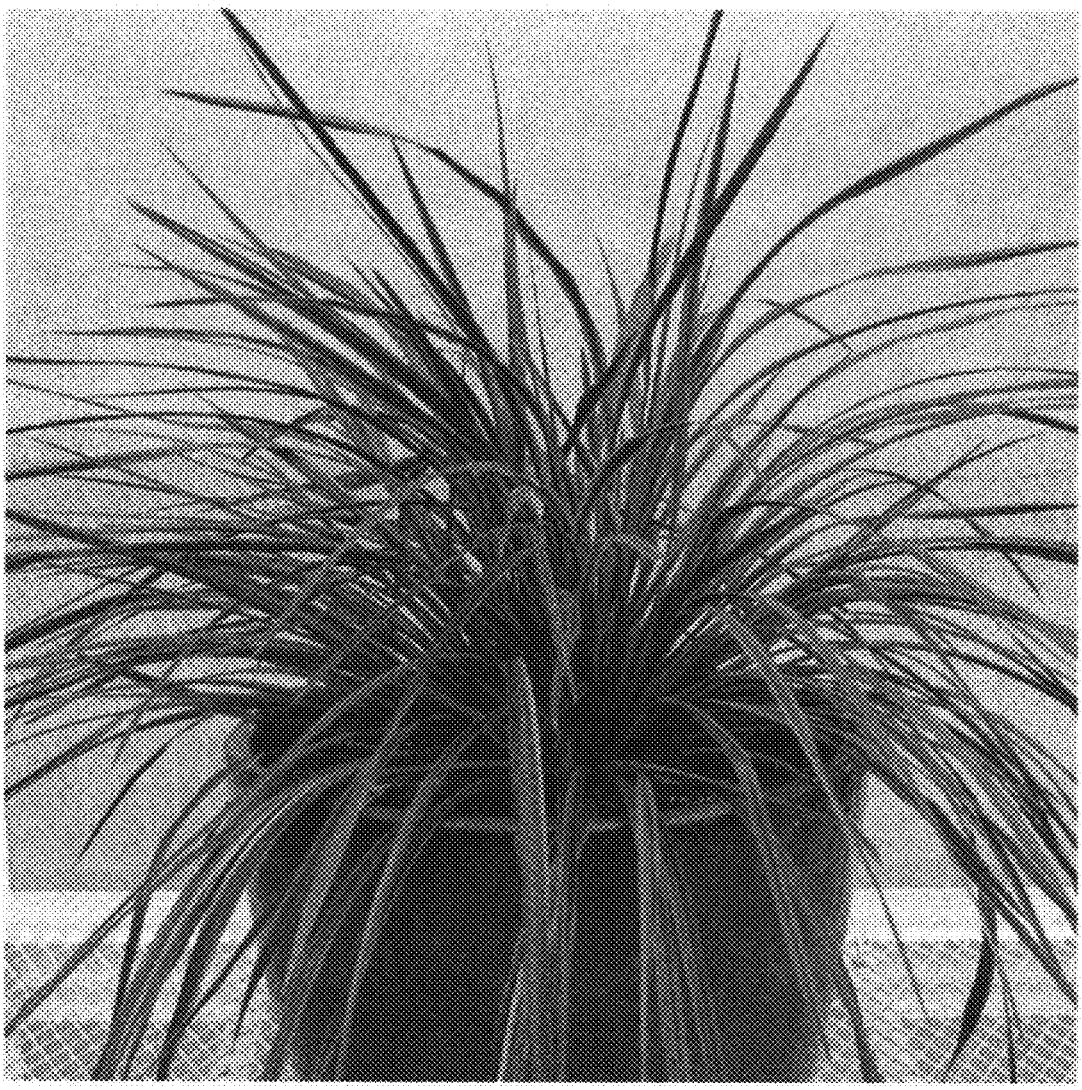

* * * * *